US 12,029,653 B1
(12) United States Patent
McLean et al.

(10) Patent No.: US 12,029,653 B1
(45) Date of Patent: Jul. 9, 2024

(54) MEDICAL IMPLANT HAVING A TEXTURED TISSUE CONTACT SURFACE

(71) Applicant: SPINE WAVE, INC., Shelton, CT (US)

(72) Inventors: Scott McLean, Sandy Hook, CT (US);
Haibo Fan, Woodbridge, CT (US);
Peter Barreiro, Trumbull, CT (US);
Daniel Vigliotti, Guilford, CT (US)

(73) Assignee: Spine Wave, Inc., Shelton, CT (US)

( * ) Notice: Subject to any disclaimer, the term of this patent is extended or adjusted under 35 U.S.C. 154(b) by 0 days.

(21) Appl. No.: 18/209,628

(22) Filed: Jun. 14, 2023

(51) Int. Cl.
A61F 2/30 (2006.01)
A61C 8/00 (2006.01)
A61F 2/28 (2006.01)
A61L 27/06 (2006.01)

(52) U.S. Cl.
CPC ........ *A61F 2/30767* (2013.01); *A61C 8/0012* (2013.01); *A61L 27/06* (2013.01); *A61F 2310/00023* (2013.01)

(58) Field of Classification Search
CPC .................... A61F 2/28; A61F 2/30767; A61F 2310/00023; A61F 2/4455; A61F 2/38; A61F 2/32; A61C 13/00; A61L 27/06
See application file for complete search history.

(56) References Cited

U.S. PATENT DOCUMENTS

| | | |
|---|---|---|
| 4,330,891 A | 5/1982 | Branemark et al. |
| 4,553,272 A | 11/1985 | Mears |
| 5,246,530 A | 9/1993 | Bugle et al. |
| 5,473,138 A | 12/1995 | Singh et al. |
| 5,603,338 A | 2/1997 | Beaty |
| 5,716,412 A | 2/1998 | DeCarlo et al. |
| 5,965,006 A | 10/1999 | Baege et al. |
| 6,419,491 B1 | 7/2002 | Ricci et al. |
| 6,951,627 B2 | 10/2005 | Li et al. |

(Continued)

FOREIGN PATENT DOCUMENTS

| | | |
|---|---|---|
| EP | 2386274 A1 | 11/2011 |
| WO | 2009046517 A1 | 4/2009 |

(Continued)

OTHER PUBLICATIONS

Dumas et al., "Femtosecond laser nano/micro patterning of titanium influences mesenchymal stem cell adhesion and commitment", Biomedical Materials, vol. 10, No. 5, Sep. 3, 2015.

(Continued)

*Primary Examiner* — Jason-Dennis N Stewart
(74) *Attorney, Agent, or Firm* — Hoffmann & Baron, LLP

(57) ABSTRACT

A medical implant has a textured tissue contact surface comprising a roughened surface that includes a plurality of macroscale and microscale projections and recesses and a plurality of nanostructures on the projections and within the recesses. The nanostructures comprise a plurality of spaced elongated waves, each wave having a crest and a trough. Each wave and recess comprise a plurality of individual polygonal structures, some of which comprise pyramidical-type shapes. The textured tissue contact surface is formed by initially laser ablating a tissue contact surface on the implant with a nanosecond pulsed laser followed by laser ablating the initially ablated surface with a femto-second pulsed laser.

28 Claims, 5 Drawing Sheets

(56) References Cited

U.S. PATENT DOCUMENTS

| | | |
|---|---|---|
| 6,979,346 B1 | 12/2005 | Hossainy et al. |
| 7,018,418 B2 | 3/2006 | Amrich et al. |
| 7,682,937 B2 | 3/2010 | Evertsen et al. |
| 7,850,862 B2 | 12/2010 | Amrich et al. |
| 8,187,255 B2 | 5/2012 | Weber et al. |
| 8,323,349 B2 | 12/2012 | Schmid |
| 8,414,654 B1 | 4/2013 | Ganey |
| 8,764,444 B2 | 7/2014 | Hansson |
| 9,125,756 B2 | 9/2015 | Ulrich et al. |
| 9,452,484 B2 | 9/2016 | Oliver Vargas |
| 9,925,295 B2 | 3/2018 | McEntire et al. |
| 10,111,753 B2 | 10/2018 | Patterson |
| 10,358,723 B2 | 7/2019 | Vaidyanathan et al. |
| 10,478,311 B2 | 11/2019 | Miccio et al. |
| 10,603,093 B2 | 3/2020 | Lin et al. |
| 11,166,824 B2 | 11/2021 | Miccio et al. |
| 11,419,735 B2 | 8/2022 | Barriero et al. |
| 2006/0000814 A1 | 1/2006 | Gu et al. |
| 2009/0082810 A1 | 3/2009 | Bhatnagar et al. |
| 2012/0312778 A1* | 12/2012 | Ullrich, Jr. .............. C23C 14/34 451/28 |
| 2012/0316650 A1 | 12/2012 | Ullrich et al. |
| 2013/0110243 A1 | 5/2013 | Patterson et al. |
| 2013/0123925 A1 | 5/2013 | Patterson et al. |
| 2018/0296343 A1 | 10/2018 | Wei |
| 2019/0076266 A1 | 3/2019 | Trudeau et al. |
| 2020/0345465 A1 | 11/2020 | Ishiwata |
| 2022/0104950 A1* | 4/2022 | Trudeau ................. B33Y 80/00 |
| 2022/0192840 A1* | 6/2022 | Barreiro ................ A61F 2/4601 |
| 2023/0130542 A1 | 4/2023 | McLean et al. |

FOREIGN PATENT DOCUMENTS

| | | |
|---|---|---|
| WO | 2013142480 A1 | 9/2013 |
| WO | 2014018325 A1 | 1/2014 |
| WO | 2016130878 A1 | 8/2016 |

OTHER PUBLICATIONS

Dumas et al., "Multiscale grooved titanium processed with femtosecond laser influences mesenchymal stem cell morphology, adhesion, and matrix organization", Journal of Biomedical Materials Research, Part A, vol. 100a (11):3108-3116, Jul. 13, 2012.

Martinez-Calderon et al., "Surface micro- and nano-texturing of stainless steel by femtosecond laser for the control of cell migration", Scientific Reports, vol. 6, 10 pages, Nov. 2, 2016.

* cited by examiner

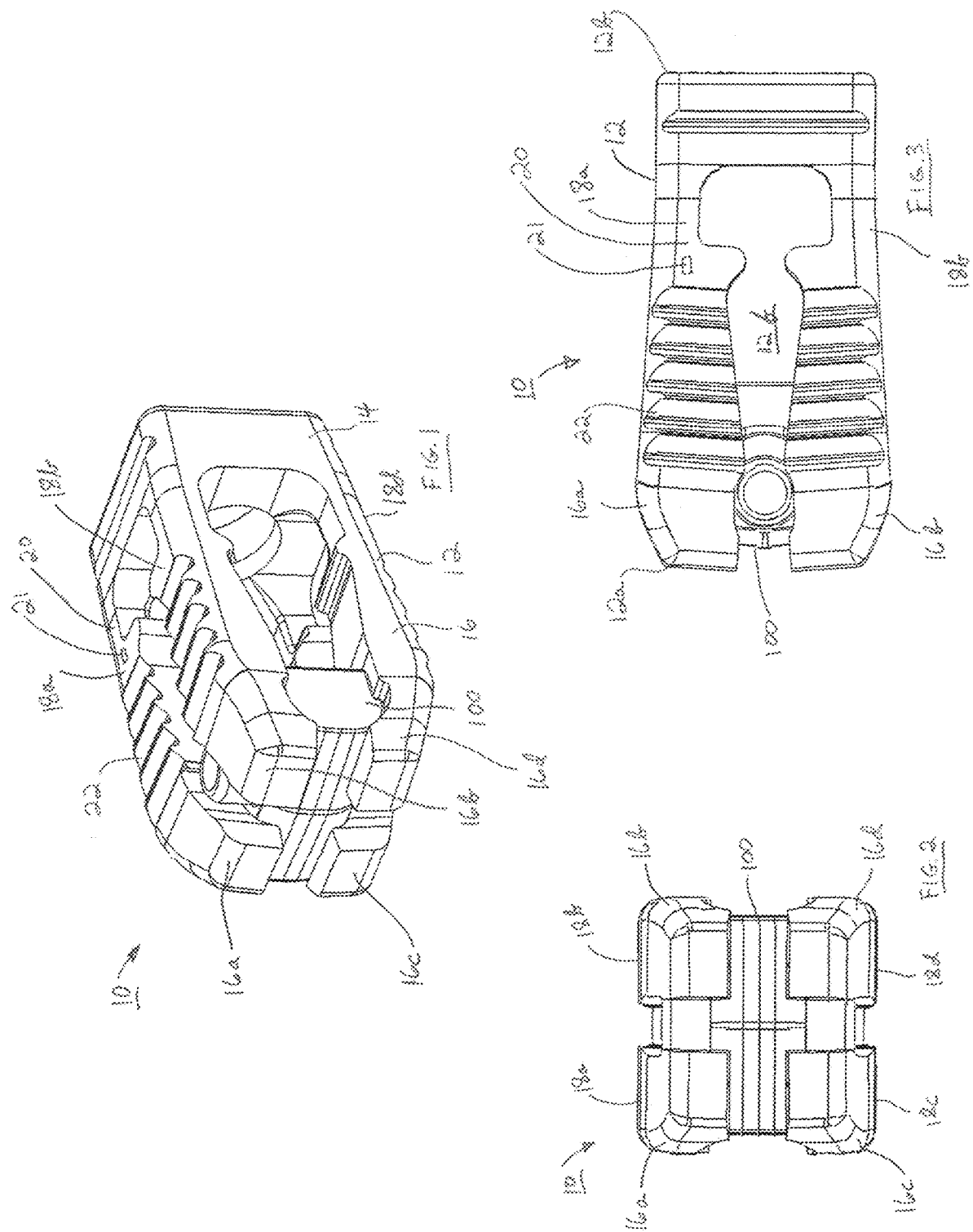

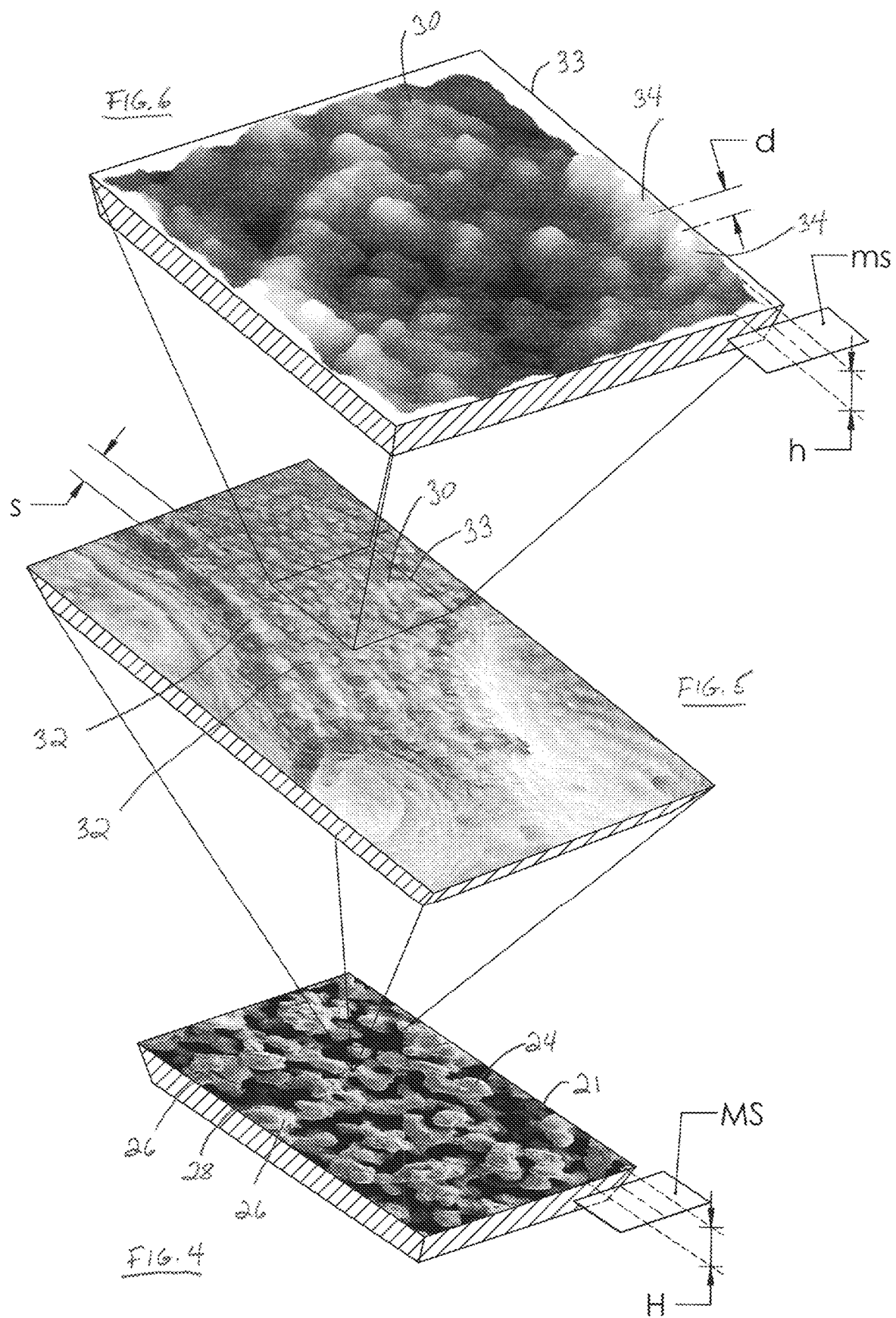

MEDICAL IMPLANT HAVING A TEXTURED TISSUE CONTACT SURFACE

FIELD OF THE INVENTION

The subject invention relates generally to the field of medical implants and more particularly to medical implants having textured tissue contact surfaces.

BACKGROUND OF THE INVENTION

It is well known in the art of medical implants to provide a roughened area on surfaces configured to contact bone or other living tissue to permit or enhance osseointegration. In osseointegration there is a direct structural and functional connection between living bone for tissue and the surface of an artificial implant. Accordingly, an implant surface that results in osseointegration whereby bone tissue can grow into the implant surface is highly desirable in bone and joint replacement techniques.

Titanium and titanium alloys are extensively used as medical implant materials, particularly for prostheses and orthopedic devices such as spinal implants, hip and knee joints and dental implants. Titanium and its alloys are essentially chosen as materials for these applications due to their highly biocompatible nature. Nevertheless, despite the biocompatible characteristics of titanium and its alloys, it has been learned that altering the topography of the implant surface can enhance the behavior of the implant increasing the likelihood of success of osseointegration.

Various technologies have been developed to create roughened titanium contact surfaces, including machined surfaces, acid-etched surfaces, grit blasted surfaces, plasma spraying surfaces, and laser ablated surfaces. The use of laser technology is particularly desirable over other prior art techniques in that the created roughened surface is integral with the implant base material and therefore avoids problems such as flaking contaminations associated with other techniques. In this regard, it has also been found that the use of a femtosecond laser produces controlled surface features with fewer thermal effects and less collateral damage than other lasers, such as nanosecond or picosecond lasers. These advantages were recognized in a publication entitled "Femtosecond Laser Nano/micro patterning of Titanium Influences Mesenchymal Stem Cell Adhesion and Commitment", by Virginia Dumas et al., Biomedical Materials, Vol. 10, no. 5, 3 Sep. 2015 (2015-09-03). Dumas concludes that a femtosecond laser produces a size of nano-ripples on titanium surfaces that promote osteoblastic differentiation with the possibility to improve osseointegration of titanium implants.

Nevertheless, Dumas understands that there is still a challenge to develop the optimal design, and that additional data are necessary to understand how the surface typography dictates the osseointegration fate of the laser treated titanium surfaces.

SUMMARY OF THE INVENTION

It is therefor an object of the invention to provide a medical implant that has an improved textured tissue contact surface.

It is a further object of the invention to provide a medical implant that has an improved textured tissue contact surface formed by a combination of nanosecond laser and femto second laser ablation.

DESCRIPTION OF THE FIGURES

FIG. 1 is a top perspective view of a medical implant incorporating a textured contact surface in accordance with a first embodiment in the form of an expandable spinal interbody fusion device.

FIG. 2 is a front elevation view of the medical implant of FIG. 1.

FIG. 3 is a top plan view of the medical implant of FIG. 1.

FIG. 4 illustrates a magnified image of a bounded portion of a roughened surface of the implant shown in FIG. 3

FIG. 5 illustrates a further magnified image of a portion of the magnified image of FIG. 4.

FIG. 6 illustrates a further magnified image of a portion of the magnified image of FIG. 5

DESCRIPTION OF THE EMBODIMENTS

Figure 7:
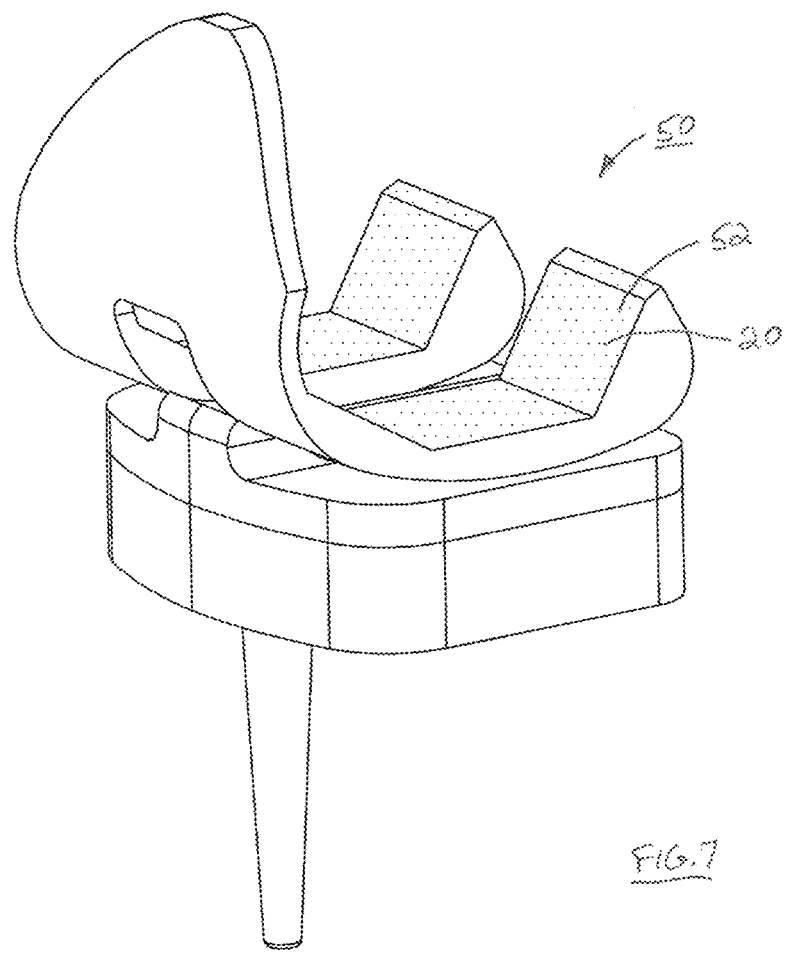
FIG. 7 is a perspective view of a medical implant incorporating a textured contact surface in accordance with a second embodiment in the form of a prosthetic device for use in knee replacement surgery.

For the purposes of promoting and understanding the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Referring now to the drawing, FIGS. 1-3 show a medical implant 10 in accordance with a first embodiment of the invention. In this embodiment, implant 10 is an expandable interbody fusion device that is sized and configured for introduction into a spinal disc space in a transforaminal lumbar interbody fusion (TLIF) procedure. Implant 10 is capable of expanding both in the vertical direction to accommodate spinal lordosis and in the lateral direction to provide sufficient structural support for opposing vertebral bodies laterally within the disc space. It should be understood that the inventive concepts described herein may be used with non-expandable as well as expandable spinal implants.

Implant 10 comprises a generally elongate cage 12 having a hollow interior 12f and a wedge 100 slidable within said hollow interior 12f. Cage 12 has a distal end 12a and a proximal end 12b. Wedge 100 is sized and configured to be slidably moved within cage 12 to expand cage 12. Cage 12 includes a base 14 at the proximal end 12b and a plurality of flexibly movable arms 16 projecting from base 14 toward distal end 12a. Arms 16 are free and unattached to each other at distal end 12a thereby allowing cage 12 to expand at its distal end 12a. In the arrangement shown, cage 12 has four movable arms 16 including a pair of upper arms 16a and 16b and a pair of lower arms 16c and 16d. Arms 16 are attached respectively to base 14 in a manner to allow deflection of arms 16 relative to base 14 in two transverse directions. In use, the transverse directions may be mutually orthogonal, namely in a vertical direction to expand the device height at distal end 12a and thereby accommodate lordosis in the disc space, and horizontally to increase the device width and hence the lateral support of opposing vertebral bodies within the disc space. Cage 10 may be formed to have a quadrangular shape, as shown in FIG. 1. Further details of the structure and function of implant 10 configured as a spinal implant are described in U.S. Pat. No. 11,419,735, entitled "Expandable TLIF Device and Related Insertion and Grafting Instrumentation", issued to Barriero et al. on Aug. 23, 2022 ("the '735 Patent"), the entire contents of which are incorporated by reference herein. The '735 Patent is assigned to the same assignee as the subject application.

Cage 12 may be formed of titanium or titanium alloys. It should be understood that cage 12 may also comprise other suitable biocompatible materials Cage 12 may be formed monolithically as a unitary structure by machining or by an additive manufacturing process, such as 3-D printing. Arms 16a and 16b have top surfaces 18a and 18b, respectively, that are configured as tissue contact surfaces for contacting endplate tissue of a superior vertebral body that defines an upper surface of the intervertebral disc space. Arms 16c and 16d have bottom surfaces 18c and 18d, respectively, that are configured as contact surfaces for contacting endplate tissue of an inferior vertebral body that defines a lower surface of the intervertebral disc space. Tissue contact surfaces 18a, 18b, 18c and 18d may be relatively smooth prior to being textured as described herein or may comprise a non-smooth surface such as a three-dimensional gyroid lattice structure as described in commonly assigned patent application, Publication No. 2023/0130542, entitled "Bellows Shaped Spinal Implant Having Gyroid Lattice Structures", published to Mclean et al. on Apr. 27, 2023, the entire contents of which are incorporated by reference herein.

In accordance with the invention, a textured surface 20 is formed on the upper and lower contact surfaces that are configured to contact endplates of opposing vertebral bodies within a spinal disc space. As such, top surfaces 18a, 18b and bottom surfaces 18c, 18d each include a textured surface 20 to provide an enhanced potential for osseointegration with tissue of the respective superior and inferior vertebral body endplates. Since the texturing of both top surfaces 18a, 18b and both bottom surfaces 18c, 18d is the same, only the details of a textured surface 20 on top surface 18a are shown and described, it being understood that the details of all the textured surfaces are the same. Textured surface 20 may be formed along the entire length of top surface 18a or, in some instances, texturing may be included only on a portion of top surface 18a, such as those portions that are configured to contact a vertebral endplate of a vertebral body. Textured surface 20 may be included on those portions of arm 16a that have fixation structures, such as a plurality of serrations 22. In other instances, no textured surfaces may be formed at the distal end 12a of cage 12 that is curved in a manner to facilitate entrance of cage 12 into the disc space.

Textured surface 20 is formed in a three-dimensional geometric pattern. FIG. 4 shows a portion 21 of textured surface 20 magnified at approximately 100× that illustrates a roughened surface 24 formed on top contact surface 18a. Roughened surface 24 includes a plurality of projections 26 and recesses 28 that define a hierarchy of macroscale and microscale structures that are tactically rough. As is commonly known and as used herein, the prefix "macro" means a dimension that is measured in millimeters (mm), which is $10^{-3}$ meters. The prefix "micro" means a dimension that is measured in microns (μm), which is $10^{-6}$ meters. The prefix "nano" means a dimension that is measured in nanometers (nm), which is $10^{-9}$ meters.

Roughened surface 24 is formed by ablating top contact surface 18a with a pulsed laser in the nanosecond range to create a plurality of projections 26 and recesses 28. Such a process may be performed in accordance with the nanosecond laser devices and methods taught and described, for example, in U.S. Pat. No. 5,473,138, entitled "Method for Increasing the Surface Area of Ceramics, Metals and Composites", issued to Singh et al on Dec. 5, 1995, the entire contents of which are incorporated herein by reference.

The height, H of the macroscale and microscale structures as shown in FIG. 4, is determined by computing the arithmetic average of the measured profile height of the surface roughness. The standard for determining roughness parameters is ISO 25178-2, which defines terms (such as Sa, Sp, Sv) and provides definitions for common surface roughness parameters. A commonly used roughness parameter is Sa, which is the arithmetic average of the absolute values of the profile height deviations from a mean surface, MS. Mean surface, MS is depicted in FIG. 4. In essence, Sa is the average of a set of individual measurements of the peaks of the projections 26 and the depths of valleys of recesses 28 as measured respectively from the mean surface, MS. The mean surface, MS is the reference surface between the peaks and valleys about which the height profile deviations to peaks and valleys are measured. The average height, $H_{avg}$, which is the difference between the peaks and valleys of the macroscale and microscale projections 26 and recesses 28, is therefore twice the arithmetic average, Sa.

Parameters of the nanosecond pulsed laser, such as the pulse duration or frequency of the laser process, or the quantity of energy applied, may be adjusted to achieve desired surface roughness of the macroscale and microscale projections 26 and recesses 28. Measurements of selected roughness characteristics may be made with a laser confocal microscope using a 5×objective lens. In a particular exemplary arrangement, parameters were adjusted to produce an arithmetic average, Sa of 37 μm, with the average height, $H_{avg}$ therefore being 74 μm, a maximum peak height, $S_p$ from the mean surface, MS of 170 μm, and a maximum valley depth, $S_v$ from the mean surface, MS of 230 μm. The maximum peak to valley height difference, $H_{max}$ is therefore $S_p$ plus $S_v$, which may thereby range up to 400 μm.

Roughened surface 24 formed on top contact surface 18a is then further laser ablated with a pulsed laser in the femtosecond range to create a plurality of nano structures 30 on the projections 26 and within the recesses 28 without interrupting the hierarchy of macrostructures and microstructures on roughened surface 24. FIG. 5 illustrates a portion of the roughened surface 24 after ablation by the femtosecond pulsed laser magnified at approximately 5000×. As illustrated, the nanostructures 30 comprise a plurality of spaced elongated ripples or waves 32. As shown in FIG. 6, which represents an atomic force microscope image of a portion 33 of the nanostructures 30 of FIG. 5 magnified at approximately 23000×, each wave 32 comprises a plurality of individual polygonal structures 34, at least some of such individual polygonal structures 34 comprising pyramidical-type shapes. It is noted as shown in FIGS. 5 and 6, that nanostructures 30 may also include individual polygonal structures 34 that are not on waves 32.

The femtosecond laser ablation may be performed with a femtosecond pulsed laser device in accordance with, for example, the methods and laser devices taught and described in U.S. 6,951,627, entitled "Method of Drilling Holes with Precision Laser Micromachining", issued October 2005 to Li et al., the entire contents of which are incorporated by reference herein. Other femtosecond pulsed lasers may also be used, such as those described in U.S. Pat. No. 10,603,093, entitled "Bone Implant and Manufacturing Method Thereof", issued on Mar. 31, 2020, to Lin et al., the contents of which are incorporated by reference in their entirety.

Parameters of the femtosecond pulsed laser may be adjusted to achieve desirable dimensions of the nanostructures 30. For example, each wave 32 has a crest defining a peak and a trough defining a valley. The primary spacing, S, which is defined as the spacing between peaks of adjacent elongated waves 32, as shown in FIG. 5, may in a particular exemplary arrangement have an average spacing, $S_{avg}$ of 1.28 µm, with a preferable range of 0.33-2.2 µm, a more preferable range of 0.64-1.92 µm, and a most preferable range of 0.96-1.60 µm. The secondary distance, d, between peaks of adjacent individual polygonal structures 34 as shown in FIG. 6 may in a particular exemplary arrangement be formed to have an average distance, $d_{avg}$ of 1.32 µm, with a preferable range of 0.79-1.84 µm, a more preferable range of 0.97-1.67 µm, and a most preferable range of 1.14-1.49 µm. Accordingly, the average primary spacing, $S_{avg}$ between peaks of adjacent elongated waves 32, and the average secondary distance, $d_{avg}$ between peaks of adjacent polygonal structures 34, are each less than 1.5 µm.

The height, h of the polygonal structures 34 as shown in FIG. 6, is determined by computing the arithmetic average, Sa of the measured profile height of the surface roughness in the same manner as described above regarding the nanosecond pulsed laser process. In this instance, Sa is the average of a set of individual measurements of the peaks and valleys of the polygonal structures 34. Mean surface, ms is the reference surface between the peaks and valleys of polygonal structures 34 about which the height profile deviations to peaks and valleys are measured. The average height, $h_{avg}$ of the polygonal structures 34 is therefore twice the arithmetic average, Sa. Thus, parameters of the femtosecond pulsed laser may be adjusted to produce polygonal structures 34 in a particular exemplary arrangement to have an arithmetic average, Sa of approximately 94 nm, resulting in an average height, $h_{avg}$ of approximately 188 nm, which is twice Sa. The range of the height profiles of the polygonal structures 34 may be determined from the average height, $S_p$ of the five highest peaks from the mean surface, ms, and the average depth, $S_v$ of the five lowest valleys from the mean surface, ms, as shown in FIG. 6. Thus, with Sa at an exemplary value of approximately 94 nm, $h_p$ may range up from mean surface, ms to 395 nm and $h_v$ may range down from mean surface, ms to 317 nm. The maximum peak to valley height difference, $h_{max}$ is therefore $S_p$ plus $S_v$, which may thereby range up to 712 nm.

Referring now to FIG. 7, a medical implant 50 is shown in accordance with a second embodiment of the invention. In this embodiment, implant 50 is a prosthetic knee implant having a bone contact surface 52. Implant 50 is used as a prosthetic device in knee replacement surgery. Implant 50 comprises a tissue contact surface 52 that is configured to contact the patient's bone and to facilitate bone growth thereto in the healing process. Contact surface 52 comprises a textured surface 20 that is formed by the nanosecond laser and femtosecond laser ablation process in the same manner as described above with respect to implant 10.

Figure 8:
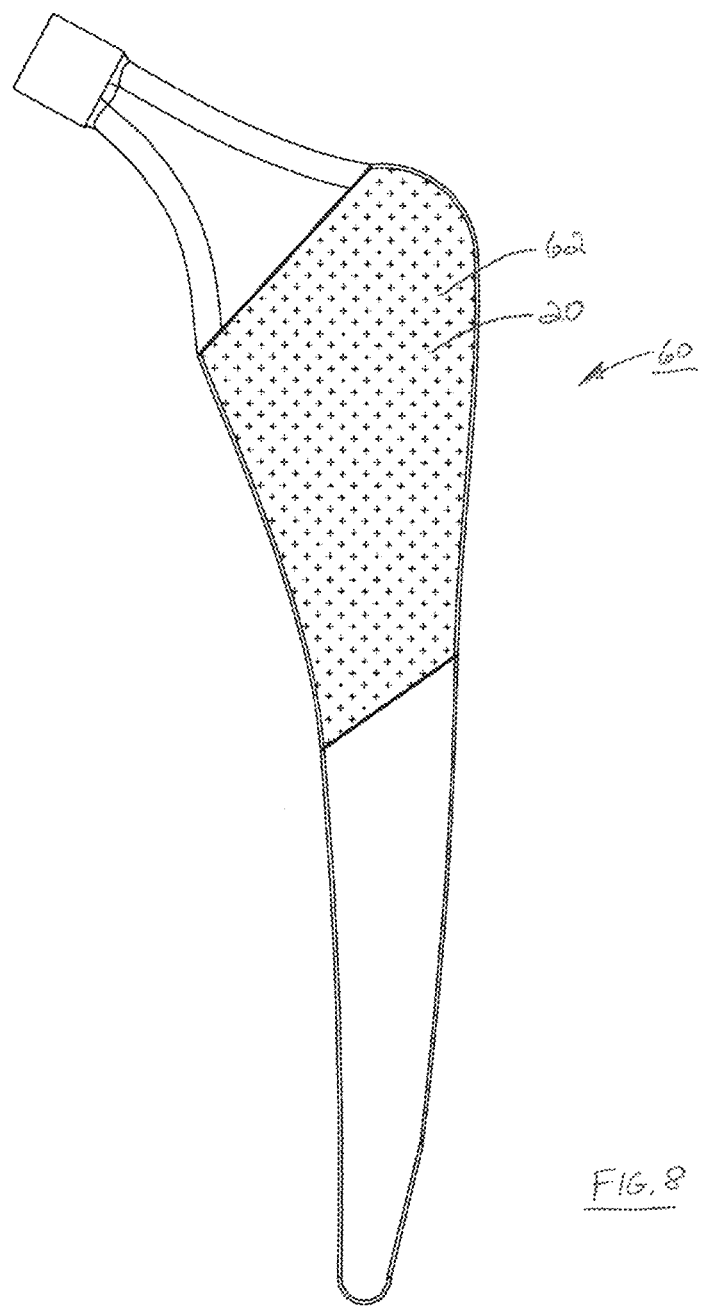
FIG. 8. is a perspective view of a medical implant incorporating a textured contact surface in accordance with a third embodiment in the form of a hip prosthesis for use in hip replacement surgery.

Referring now to FIG. 8, a medical implant 60 is shown in accordance with a third embodiment of the invention. In this embodiment, implant 60 is a hip prosthesis that is used in hip replacement surgery. Implant 60 comprises a tissue contact surface 62 that is configured to contact the patient's hip bone and to facilitate bone growth thereto in the healing process. Contact surface 62 comprises a textured surface 20 that is formed by the nanosecond laser and femtosecond laser ablation process in the same manner as described above with respect to implant 10.

Figure 9:
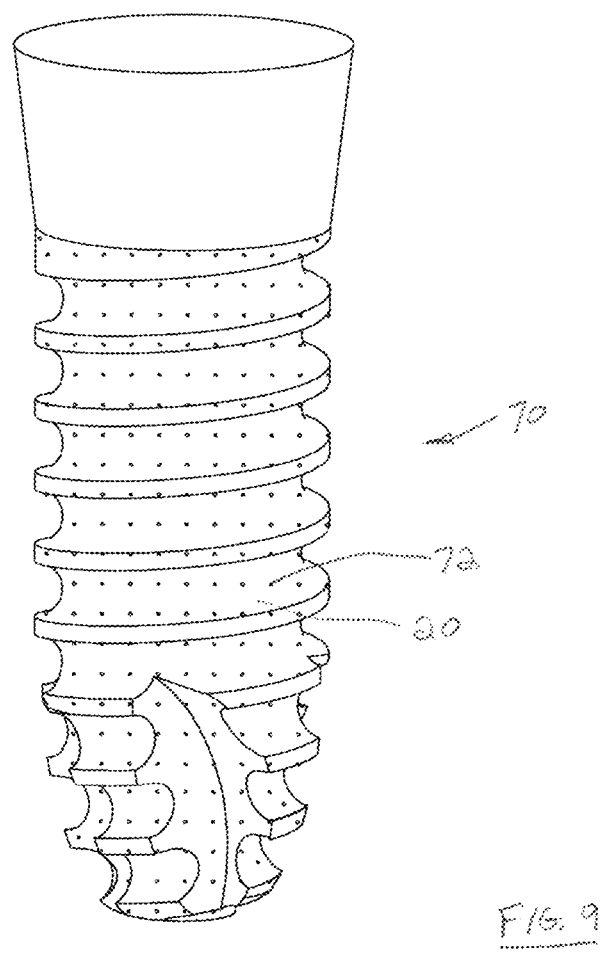
FIG. 9 is a perspective view of a medical implant incorporating a textured contact surface in accordance with a fourth embodiment in the form of a dental implant configured for insertion into a human jawbone.

Referring now to FIG. 9, a medical implant 70 is shown in accordance with a fourth embodiment of the invention. In this embodiment, implant 70 is a dental fixture configured for insertion into a human jawbone during dental surgery. Implant 70 comprises a tissue contact surface 72 that is configured to contact the patient's jawbone and to facilitate bone growth thereto in the healing process. Contact surface 72 comprises a textured surface 20 that is formed by the nanosecond laser and femtosecond laser ablation process in the same manner as described above with respect to implant 10.

While the invention has been illustrated and described in detail in the drawings and foregoing description, the same should be considered as illustrative and not restrictive in character. Accordingly, it is understood that only the preferred embodiments have been presented and that all changes, modifications and further applications that come within the spirit of the invention are desired to be protected.

What is claimed is:

1. A medical implant comprising a textured tissue contact surface, said textured tissue contact surface comprising:
   a roughened surface on said tissue contact surface that includes a plurality of macroscale and microscale projections and recesses; and
   a plurality of nanostructures on said projections and within said recesses, said nanostructures comprising a plurality of elongated waves, each wave having a crest and a trough, said crests extending along rows of elongated waves that are laterally spaced from each other.

2. The medical implant of claim 1, wherein said implant is formed of titanium or a titanium alloy.

3. The medical implant of claim 1, wherein said implant is a spinal interbody fusion device.

4. The medical implant of claim 1, wherein said implant is a knee prosthesis.

5. The medical implant of claim 1, wherein said implant is a hip prosthesis.

6. The medical implant of claim 1, wherein said implant is a dental implant.

7. A medical implant comprising a textured tissue contact surface, said medical implant comprising titanium or titanium alloys, said textured tissue contact surface being prepared by a process comprising the steps of:
   initially laser ablating said tissue contact surface on said implant with a nanosecond pulsed laser to form a roughened surface on said tissue contact surface that includes a hierarchy of macrostructures and microstructures that are tactically rough; and
   then laser ablating said roughened surface with a femtosecond pulsed laser to form a plurality of nanostructures on said roughened surface without interrupting the hierarchy of macrostructures and microstructures.

8. The medical implant of claim 7, wherein said hierarchy of macrostructures and microstructures comprises a plurality of projections and recesses, and wherein said nanostructures comprise a plurality of spaced elongated waves and a plurality of individual polygonal structures on said projections and within said recesses, each wave having a crest and a trough and including some of said individual polygonal structures.

9. The medical implant of claim 8, wherein at least some of said plurality of individual polygonal structures comprise pyramidical-type shapes.

10. The medical implant of claim 8, wherein said plurality of projections and recesses have an average height, $H_{avg}$, and wherein said plurality of polygonal structures have an average height, $h_{avg}$, and wherein $H_{avg}$ is greater than $h_{avg}$.

11. The medical implant of claim 10, wherein said plurality of projections and recesses have a maximum height, $H_{max}$, and wherein said plurality of polygonal structures have a maximum height, $h_{max}$, and wherein $H_{max}$ is greater than $h_{max}$.

12. The medical implant of claim 11, wherein the average spacing, $S_{avg}$ between peaks of said elongated waves, and the average distance, $d_{avg}$ between peaks of said adjacent polygonal structures are each less than 1.5 μm.

13. The medical implant of claim 11, wherein the maximum spacing, S between peaks of said elongated waves is greater than the maximum distance, d between peaks of said adjacent polygonal structures.

14. The medical implant of claim 13, wherein the maximum spacing, S between peaks of said elongated waves is 2.2 μm, and the maximum distance, d between peaks of said adjacent polygonal structures is 1.84 μm.

15. The medical implant of claim 13, wherein the minimum spacing, S between peaks of said elongated waves is less than the minimum distance, d between peaks of said adjacent polygonal structures.

16. The medical implant of claim 15, wherein the minimum spacing, S between peaks of said elongated waves is 0.33 μm, and the minimum distance, d between peaks of said adjacent polygonal structures is 0.79 μm.

17. The medical implant of claim 15, wherein said implant is a spinal interbody fusion device.

18. The medical implant of claim 15, wherein said implant is a knee prosthesis.

19. The medical implant of claim 15, wherein said implant is a hip prosthesis.

20. The medical implant of claim 15, wherein said implant is a dental implant.

21. A medical implant comprising a textured tissue contact surface, said medical implant comprising titanium or titanium alloys, said textured tissue contact surface comprising:

a roughened surface on said tissue contact surface that includes a plurality of macroscale and microscale projections and recesses, each of said projections including a peak and each of said recesses including a valley, said plurality of projections and recesses having an average peak to valley height, Havg; and a plurality of nanostructures on said projections and within said recesses, said nanostructures comprising a plurality of spaced elongated waves and a plurality of individual polygonal structures, some of said polygonal structures being included on said elongated waves, said polygonal structures each including a peak and a valley therebetween, said plurality of polygonal structures having an average peak to valley height, $h_{avg}$, wherein $H_{avg}$ is greater than $h_{avg}$.

22. The medical implant of claim 21, wherein at least some of said plurality of individual polygonal structures comprise pyramidical-type shapes.

23. The medical implant of claim 21, wherein said plurality of projections and recesses have a maximum height, $H_{max}$, and wherein said plurality of polygonal structures have a maximum height, $h_{max}$, and wherein $H_{max}$ is greater than $h_{max}$.

24. The medical implant of claim 21, wherein the average spacing, $S_{avg}$ between peaks of said elongated waves, and the average distance, $d_{avg}$ between peaks of said adjacent polygonal structures are each less than 1.5 μm.

25. The medical implant of claim 21, wherein the maximum spacing, S between peaks of said elongated waves is greater than the maximum distance, d between peaks of said adjacent polygonal structures.

26. The medical implant of claim 25, wherein the maximum spacing, S between peaks of said elongated waves is 2.2 μm, and the maximum distance, d between peaks of said adjacent polygonal structures is 1.84 μm.

27. The medical implant of claim 21, wherein the minimum spacing, S between peaks of said elongated waves is less than the minimum distance, d between peaks of said adjacent polygonal structures.

28. The medical implant of claim 9, wherein the minimum spacing, S between peaks of said elongated waves is 0.33 μm, and the minimum distance, d between peaks of said adjacent polygonal structures is 0.79 μm.

\* \* \* \* \*